United States Patent
MacDonald

(10) Patent No.: US 9,677,013 B2
(45) Date of Patent: Jun. 13, 2017

(54) METHOD FOR PRODUCING BASE LUBRICATING OIL FROM OILS RECOVERED FROM COMBUSTION ENGINE SERVICE

(71) Applicant: PNG GOLD CORPORATION, Vancouver (CA)

(72) Inventor: Martin R. MacDonald, Plano, TX (US)

(73) Assignee: PNG Gold Corporation, West Vancouver (CA)

( * ) Notice: Subject to any disclaimer, the term of this patent is extended or adjusted under 35 U.S.C. 154(b) by 0 days.

(21) Appl. No.: 14/201,165

(22) Filed: Mar. 7, 2014

(65) Prior Publication Data

US 2014/0251869 A1    Sep. 11, 2014

Related U.S. Application Data

(63) Continuation of application No. 14/169,126, filed on Jan. 30, 2014.

(60) Provisional application No. 61/774,037, filed on Mar. 7, 2013, provisional application No. 61/774,027, filed on Mar. 7, 2013.

(51) Int. Cl.

| | | |
|---|---|---|
| C10G 67/04 | (2006.01) |
| C10G 53/04 | (2006.01) |
| C07C 5/02 | (2006.01) |
| C07C 7/00 | (2006.01) |
| C10G 21/16 | (2006.01) |
| C10G 21/18 | (2006.01) |
| C10G 21/20 | (2006.01) |
| C10G 21/24 | (2006.01) |
| C10G 45/04 | (2006.01) |
| C10G 67/14 | (2006.01) |
| C10G 21/02 | (2006.01) |
| C10G 7/00 | (2006.01) |
| C10G 21/00 | (2006.01) |

(52) U.S. Cl.
CPC ............ *C10G 53/04* (2013.01); *C07C 5/02* (2013.01); *C07C 7/005* (2013.01); *C10G 7/00* (2013.01); *C10G 7/003* (2013.01); *C10G 7/006* (2013.01); *C10G 21/006* (2013.01); *C10G 21/02* (2013.01); *C10G 21/16* (2013.01); *C10G 21/18* (2013.01); *C10G 21/20* (2013.01); *C10G 21/24* (2013.01); *C10G 45/04* (2013.01); *C10G 67/04* (2013.01); *C10G 67/14* (2013.01); *C10G 2300/1007* (2013.01)

(58) Field of Classification Search
CPC .................................................... C10G 67/04
See application file for complete search history.

(56) References Cited

U.S. PATENT DOCUMENTS

| | | | |
|---|---|---|---|
| 2,081,601 A * | 5/1937 | Ridgway | B01D 3/4261 196/132 |
| 2,875,139 A * | 2/1959 | Little | B01D 3/06 196/128 |
| 3,173,859 A | 3/1965 | Chambers | |
| 3,625,881 A | 12/1971 | Chambers | |
| 3,923,644 A | 12/1975 | Hindman | |
| 4,021,333 A | 5/1977 | Habiby et al. | |
| 4,033,859 A | 7/1977 | Davidson et al. | |
| 4,071,438 A | 1/1978 | O'Blassny | |
| 4,101,414 A | 7/1978 | Kim et al. | |
| 4,151,072 A | 4/1979 | Nowack et al. | |
| 4,169,044 A | 9/1979 | Crowley | |
| 4,233,140 A | 11/1980 | Antonelli et al. | |
| 4,302,325 A | 11/1981 | Fletcher et al. | |
| 4,342,645 A | 8/1982 | Fletcher et al. | |
| 4,360,420 A | 11/1982 | Fletcher et al. | |
| 4,399,025 A | 8/1983 | Fletcher et al. | |

(Continued)

FOREIGN PATENT DOCUMENTS

| | | |
|---|---|---|
| CA | 2351606 | 5/2000 |
| CA | 2600328 | 9/2006 |

(Continued)

OTHER PUBLICATIONS

"Standard Guide for Characterizing Hydrocarbon Lubricant Base Oils", The American Society for Testing and Materials, ASTM D6074-08, Nov. 2008.

(Continued)

*Primary Examiner* — Randy Boyer
(74) *Attorney, Agent, or Firm* — MBM Intellectual Property Law LLP

(57) ABSTRACT

A method for producing ILSAC GF5 or higher compatible oils from used oil, comprising separating material having a boiling point less than about 350° F. from recovered oil to produce de-volatized oil fraction and light oil fraction. Separating material with a boiling point greater than about 350° F. and less than about 650° F. from the de-volatized oil fraction to produce fuel oil fraction and heavy oil fraction. Separating material with a boiling point greater than about 1200° F. from the heavy oil fraction to produce partially purified oil fraction and residual fraction. Treating the partially purified oil fraction to separate it into purified oil fraction and contaminant fraction. Hydrogenating the contaminant fraction to remove predetermined compounds, further saturating the fraction and thereby creating a saturated oil fraction. Fractionating the saturated oil stream to produce one or more of naphtha fraction, diesel oil fraction and base oil fraction.

28 Claims, 4 Drawing Sheets

(56) References Cited

U.S. PATENT DOCUMENTS

| | | |
|---|---|---|
| 4,431,524 A | 2/1984 | Norman |
| 4,432,865 A | 2/1984 | Norman |
| 4,512,878 A | 4/1985 | Reid et al. |
| 4,624,746 A * | 11/1986 | Hiramatsu ............. B01D 3/425 196/132 |
| 4,894,140 A | 1/1990 | Schon |
| 4,894,145 A * | 1/1990 | Jensen ................. B01D 3/4244 202/160 |
| 4,941,967 A | 7/1990 | Mannetje et al. |
| 5,028,313 A | 7/1991 | Kalnes et al. |
| 5,045,179 A | 9/1991 | Langhoff et al. |
| 5,049,258 A | 9/1991 | Keim et al. |
| 5,102,531 A | 4/1992 | Kalnes et al. |
| 5,143,597 A | 9/1992 | Sparks et al. |
| 5,242,579 A | 9/1993 | Mead et al. |
| 5,244,565 A | 9/1993 | Lankton et al. |
| 5,302,282 A | 4/1994 | Kalnes et al. |
| 5,306,419 A | 4/1994 | Harrison et al. |
| 5,362,381 A | 11/1994 | Brown et al. |
| 5,382,328 A | 1/1995 | Drespa et al. |
| 5,384,037 A | 1/1995 | Kalnes |
| 5,447,628 A | 9/1995 | Harrison et al. |
| 5,632,867 A | 5/1997 | Davis et al. |
| 5,707,510 A | 1/1998 | Berry |
| 5,759,385 A | 6/1998 | Aussillous et al. |
| 5,795,462 A | 8/1998 | Shurtleff |
| 5,814,207 A | 9/1998 | Kenton |
| 5,843,384 A | 12/1998 | Aussillous et al. |
| 5,871,618 A | 2/1999 | Lee et al. |
| 5,885,444 A | 3/1999 | Wansborough et al. |
| 5,904,838 A | 5/1999 | Kalnes et al. |
| 5,980,698 A | 11/1999 | Abrosimov et al. |
| 6,007,701 A | 12/1999 | Sherman et al. |
| 6,106,699 A | 8/2000 | MacDonald et al. |
| 6,117,309 A | 9/2000 | Daspit et al. |
| RE36,922 E | 10/2000 | Sparks et al. |
| 6,132,596 A | 10/2000 | Yu |
| 6,174,431 B1 | 1/2001 | Williams et al. |
| 6,179,999 B1 | 1/2001 | Sherman et al. |
| 6,238,551 B1 | 5/2001 | Sherman et al. |
| 6,292,737 B1 | 9/2001 | Higashimata et al. |
| 6,319,394 B2 | 11/2001 | Sherman et al. |
| 6,320,090 B1 | 11/2001 | Sherman et al. |
| 6,372,122 B1 | 4/2002 | Gorman |
| 6,398,948 B1 | 6/2002 | Sherman et al. |
| 6,402,937 B1 | 6/2002 | Shaffer, Jr. et al. |
| 6,440,298 B1 | 8/2002 | Shurtleff |
| 6,512,147 B2 | 1/2003 | Inaba et al. |
| 6,592,748 B2 | 7/2003 | Cody et al. |
| RE38,366 E | 12/2003 | Kenton |
| 6,712,954 B1 | 3/2004 | Pohler et al. |
| 6,805,062 B2 | 10/2004 | Shurtleff |
| 6,929,737 B2 | 8/2005 | Sherman et al. |
| 7,226,533 B2 | 6/2007 | Aramburu |
| 7,261,808 B2 | 8/2007 | Grandvallet et al. |
| 7,267,760 B2 | 9/2007 | Sherman et al. |
| 8,366,912 B1 | 2/2013 | MacDonald |
| 2001/0001198 A1 | 5/2001 | Sherman et al. |
| 2001/0022281 A1 | 9/2001 | Sherman et al. |
| 2001/0025807 A1 | 10/2001 | Sherman et al. |
| 2002/0036158 A1 | 3/2002 | Austin |
| 2004/0011704 A1 | 1/2004 | Shurtleff |
| 2005/0006282 A1 | 1/2005 | Grandvallet et al. |
| 2008/0000808 A1 | 1/2008 | Sherman et al. |

FOREIGN PATENT DOCUMENTS

| | | |
|---|---|---|
| CA | 2600328 A1 * | 9/2006 |
| WO | 99/13033 | 3/1999 |
| WO | 00/53706 | 9/2000 |

OTHER PUBLICATIONS

"Engine Oil Licensing and Certification Systems Specification", American Petroleum Institute, API 1509, 14th Edition, Dec. 1996.
Canadian Patent Office; International Search Report and Written Opinion; PCT Application No. PCT/IB2014/000485; Jul. 18, 2014, 13 pages.
Canadian Patent Office; Office Action; Canadian Patent Application No. 2,845,173, May 23, 2014; 7 pages.

* cited by examiner

METHOD FOR PRODUCING BASE LUBRICATING OIL FROM OILS RECOVERED FROM COMBUSTION ENGINE SERVICE

RELATED APPLICATIONS

The present application claims priority to U.S. Provisional patent application 61/774,027, filed Mar. 7, 2013 and U.S. Provisional patent application 61/774,037, filed Mar. 7, 2013, and is related to U.S. Pat. No. 8,366,912, issued Feb. 5, 2013, which are hereby incorporated by reference for all purposes as if set forth herein in their entirety.

TECHNICAL FIELD

The present disclosure relates to the recovery of synthetic oils, and more specifically to the recovery of base lubricating oils from oils removed from combustion engine service.

BACKGROUND OF THE INVENTION

Large volumes of engine oil is produced world-wide, but is discarded after use.

SUMMARY OF THE INVENTION

A method for producing International Lubricant Standardization and Approval Committee (ILSAC) GF5 or higher compatible oils from used oil is disclosed. The method includes separating material having a boiling point of less than about 350° F. from recovered oil to produce a de-volatized oil fraction and a light oil fraction. Separating material with a boiling point of greater than about 350° F. and less than about 650° F. from the de-volatized oil fraction to produce a fuel oil fraction and a heavy oil fraction. Separating material with a boiling point of greater than about 1200° F. from the heavy oil fraction to produce a partially purified oil fraction and a residual fraction. Treating the partially purified oil fraction to separate it into purified a oil fraction and a contaminant fraction. Hydrogenating the contaminant fraction to remove predetermined compounds, further saturating the fraction and thereby creating a saturated oil fraction. Fractionating the saturated oil stream to produce one or more of a naphtha fraction, a diesel oil fraction and a base oil fraction.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE SEVERAL VIEWS OF THE DRAWINGS

Aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views, and in which.

DETAILED DESCRIPTION OF THE INVENTION

Figure 1:
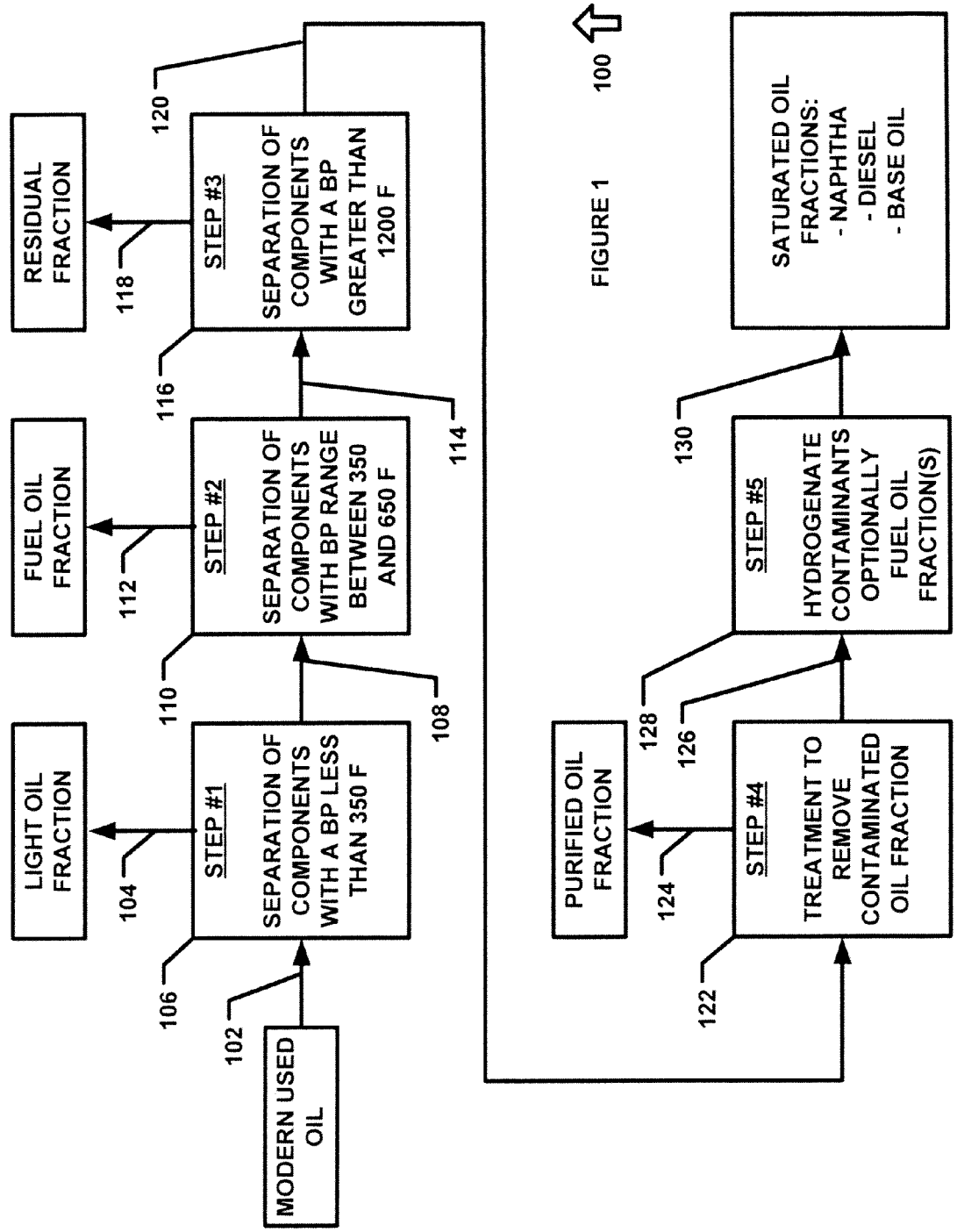
FIG. 1 is a diagram of a system for processing waste oil in accordance with an exemplary embodiment of the present disclosure.

In the description that follows, like parts are marked throughout the specification and drawings with the same reference numerals. The drawing figures might not be to scale and certain components can be shown in generalized or schematic form and identified by commercial designations in the interest of clarity and conciseness.

The present disclosure relates to producing high quality petroleum products suitable for modern environmentally friendly and technologically enhanced engines from spent modern engine oils consisting in part of synthetic oils. The disclosed process includes separating the feedstock into a volatile fraction, a fuel oil fraction, a residual fraction, and a partially purified oil fraction, and thereafter treating the partially purified oil to separate it into a purified oil fraction and a contaminant fraction. The contaminant fraction is hydrogenated to upgrade this fraction and produce a saturated oil fraction. The petroleum products produced by this process are greater than the quantity and higher in quality than those produced by previous processes.

In recent years, the demand for lubricating oils for combusting engines has increased, such that conventional lubricants are no longer suitable for use in today's modern combustion engines. As a result, the need for synthetic quality and specialized lubricants has increased to satisfy these demands. In addition to being more robust and capable of handling modern extreme service conditions, these new lubricants produce less emissions and yield longer service lifetimes. As a result of the characteristics of these improved oils, new processes are needed to treat the spent oils once they have been recovered at the end of their service life.

Historically, several treatment processes have been proposed for treating conventional crude oil-based used oil, which produce conventional products which heretofore have satisfied lower lubricant standards. However, the new synthetic lubricants that are being produced including poly aromatics and esters that were not typically found in used oils until recently. Furthermore, the increasingly stringent lubricant specification, such as ILSAC GF5, has resulted in a change to many chemical additives that are compounded with the base oils. As a result, these new lubricants, when recovered after service, can pose processing challenges for some of the traditional recovery technologies.

Conventional oils recovered from combustion engine services can be re-refined utilizing a process known as hydrotreating or hydrofinishing. This treatment method typically employs some form of distillation to separate a gas oil fraction from other contaminants, followed by treatment with hydrogen at elevated temperatures and pressures over a catalyst. While this method has been successful in saturating some aromatics and non-saturated compounds, severe hydrotreating (such as characterized by higher temperatures, higher pressures, greater hydrogen concentrations, and longer residence time) is required to sufficiently saturate oil molecules and achieve the physical and compositional properties of higher quality base oils. Unfortunately, these severe processing conditions can result in molecular cracking, which consequently results in damage to synthetic oil molecules thereby lowering the quality and amount of base oil produced. Furthermore, when higher quality molecules, such as modern synthetic oils, are processed through hydrotreating, the molecules are susceptible to being fractured or changed, making them less desirable or unsuitable for use in manufacturing GF5 lubricants.

Another method of re-refining oils recovered from combustion engine service utilizes solvent extraction. These processes suffer from a yield/quality trade-off. In solvent extraction, a portion of the contaminated base oil molecules (polars, aromatics, heteroatoms, unsaturates) are separated from the base oil fraction using liquid/liquid extraction. This process creates a purified base oil stream (raffinate) and an extract oil stream (extract) wherein some of the contaminated molecules are concentrated. The efficacy of separation of quality base oil from contaminated molecules is determined by several variables including temperature, treatment ratio, residence time, contact, and the presence of other fluids added to the oil and solvent. In the extraction process, there is continual trade-off between selectivity (the amount of good base oil taken with the extract) and purity (percent of contaminated base oil molecules left in the raffinate).

Typically, solvent extraction processes are effective at removing some of the aromatics, polars and unsaturated compounds. However, to reach the desired level of purification necessary for higher quality standards using known processes, the selectivity of the solvent must be reduced whereby both contaminated molecules as well as good molecules are dissolved in the solvent, which significantly reduces the yield of base oil. Therefore, there is an inherent trade-off between quality and yield so that in order to get high quality base oil, yield quantity is reduced.

As previously noted, known processes of this type are capable of producing either quality or yield, but not both. This is due the nature of the oils recovered from combustion engine service, which consists of a wide variety of types, qualities and contaminants and the consequential trade-off between quality and quantity that is typically inherent in these processes. Furthermore, most known processes of this type typically can only produce an API Group I base oil. An additional disadvantage of this process is that the extract formed by solvent extraction of oils recovered from combustion engine service is also prone to reformation assumed to be polymerization. This polymerization is believed to be catalyzed by acid, which can be reduced through addition of base or blending with fuel oil or other anti-polymer chemicals, thereby adding to the overall production cost. Furthermore, the resulting product is low quality fuel oil, which may be difficult to market.

The present disclosure provides a system and method for producing high quality petroleum products suitable for modern environmentally friendly and technology enhanced engines, such as on-road diesel fuel and GF5 compatible base oils, from used engine oils consisting in part of synthetic oils. The process includes separating the feedstock into a volatile fraction, a fuel oil fraction, a residual fraction, and a partially purified oil fraction, and thereafter treating the partially purified oil to separate it into a purified oil fraction and a contaminant fraction, then hydrogenating the contaminant fraction to upgrade this fraction and produce a saturated oil fraction. Finally, the saturated oil fraction is fractionated to produce a naphtha stream, a diesel fuel stream and one or more base oil streams. The petroleum products produced by this process are greater in quantity and higher in quality than those produced by previous processes.

The present disclosure further relates to a method for efficiently producing a high yield of ILSAC GF5 or higher compatible oils and on-road diesel fuel from the recovery and upgrade of oil (feedstock) derived from modern electric, hybrid, turbocharged, and high efficiency gasoline and diesel engines. In one exemplary embodiment, the method can include first separating at least a portion of the feedstock with a boiling point less than about 350° F. from the recovered oil to produce a de-volatized oil fraction and a light oil fraction. Second, at least a portion of the feedstock is separated with a boiling point greater than about 350° F. and less than about 650° F. from the de-volatized oil fraction to produce a fuel oil fraction and a heavy oil fraction. Third, at least a portion of the feedstock is separated with a boiling point greater than about 1200° F. from the heavy oil fraction creating a partially purified oil fraction and a residual fraction. Fourth, the partially purified oil fraction is treated to separate it into a purified oil fraction and a contaminant fraction. Fifth, the contaminant fraction is hydrogenated, or optionally the combined contaminant fraction and fuel oil fraction is hydrogenated, to improve or remove undesirable constituents further saturating the fraction(s) and thereby creating a saturated oil fraction. Then the saturated oil stream is fractionated to produce a naphtha fraction, a diesel oil fraction and a base oil fraction. Optionally, the purified oil stream can be fractionated to produce two or more purified oil streams that are differentiated based on boiling point profiles.

FIG. 1 is a diagram of a system 100 for processing waste oil in accordance with an exemplary embodiment of the present disclosure. In the embodiment shown, oil recovered from combustion engine service, line 102, is first charged to separation zone 106 of step 1 where a light oil fraction, line 104, is separated from the de-volatilized oil fraction, line 108. The materials recovered through line 104 may be low molecular weight materials such as light hydrocarbons, water, glycols, and the like, typically having a boiling range generally below about 350° F. The average residence time through this section 3 is generally between about 5 minutes and 10 hours. In step 2, the de-volatilized oil, line 108, is then charged to a second separation zone 110 where a fuel oil fraction, line 112, is separated from a heavy oil fraction, line 114. The fuel oil fraction consists primarily of hydrocarbons with a boiling point greater than 350° F. and less than 650° F. The average residence time through this section is between about 30 minutes and 10 hours. In a third step, the heavy oil fraction, line 114, is then passed to a third separation zone 116 where a residual fraction, line 118, is separated from a partially purified oil fraction, line 120. The residual fraction, line 118, consists primarily of non-volatile material and material with a boiling point in excess of 1200° F. The partially purified oil is recovered through a line 120 and typically consists of hydrocarbon molecules with 18 to 60 carbon atoms and typically having a boiling range (between) from about 650° F. to about 1200° F.

In a separation zone 122 of the fourth step, a portion of the non-paraffinic or unsaturated molecules, such as the aromatics, olefins, and heteroatoms (contaminant fraction), are separated from the paraffinic oil through a line 126 and passed to a treatment section 128 in the fifth step. The primarily paraffinic material is recovered through line 124 and sold as a blend stock for the production of ILSAC GF5 or higher quality oils. The contaminant fraction recovered through line 126 is passed to a treatment zone 128 of step 5 where it is treated with hydrogen to more fully saturate the molecules and produce a more saturated oil fraction, line 130. The saturated oil fraction is then distilled to produce a naphtha fraction, diesel oil ion and one or more base oil fractions.

In the first three steps, zones 106, 110 and 116, the partially purified oil action is separated from various physical and chemical contaminants. Typically, such contaminants include water, light hydrocarbons, extractants, solids, polymers, high molecular weight hydrocarbons, lubricating oil additives, chemicals, salts, dirt, fines, debris, non-volatiles, and the like. Several processes or combination of processes can be used to effect these separations including various forms of extraction, distillation, filtration, centrifugation, adsorption, and the like, as known to those skilled in the art. Typically, the separation will take place based upon differences in the physical or chemical properties of the base oil fraction and the various contaminating materials. In the fourth step, the partially purified oil fraction is then fed to zone 122 of the process where a portion of the non-paraffinic material is separated from the paraffinic material. These molecules may comprise polars, aromatics, olefins, unsaturates, heteroatoms, and the like, which are separated from the higher quality base oil molecules, which are typically saturated, paraffinic and non-aromatic. The purified oil fraction line 124 is a high quality oil stream typically having a percent of saturates greater than 90% and a sulfur content of less than about 0.3 weight percent. The stream in line 126 will typically have a higher concentration of sulfur, oxygen, nitrogen, olefins, aromatics, and the like. Various processes or combinations thereof can be used to effect separation of these materials from the high quality base oil. These processes include various forms of extraction, ultrafiltration, absorption, molecular sieves, and the like, as known to those skilled in the art. In the fifth step, stream 126 is processed in zone 128 by hydrogenating, alkylating, molecular reforming, molecular substituting, or the like, or a combination thereof, as known to those skilled in the art, to remove undesirable elements such as sulfur, nitrogen, oxygen, and the like, and increase the percent saturation of at least a portion of the hydrocarbon molecules. The resulting saturated oils produced through line 130 are typically sold as a petroleum product suitable for combustion or lubrication use.

Figure 2:
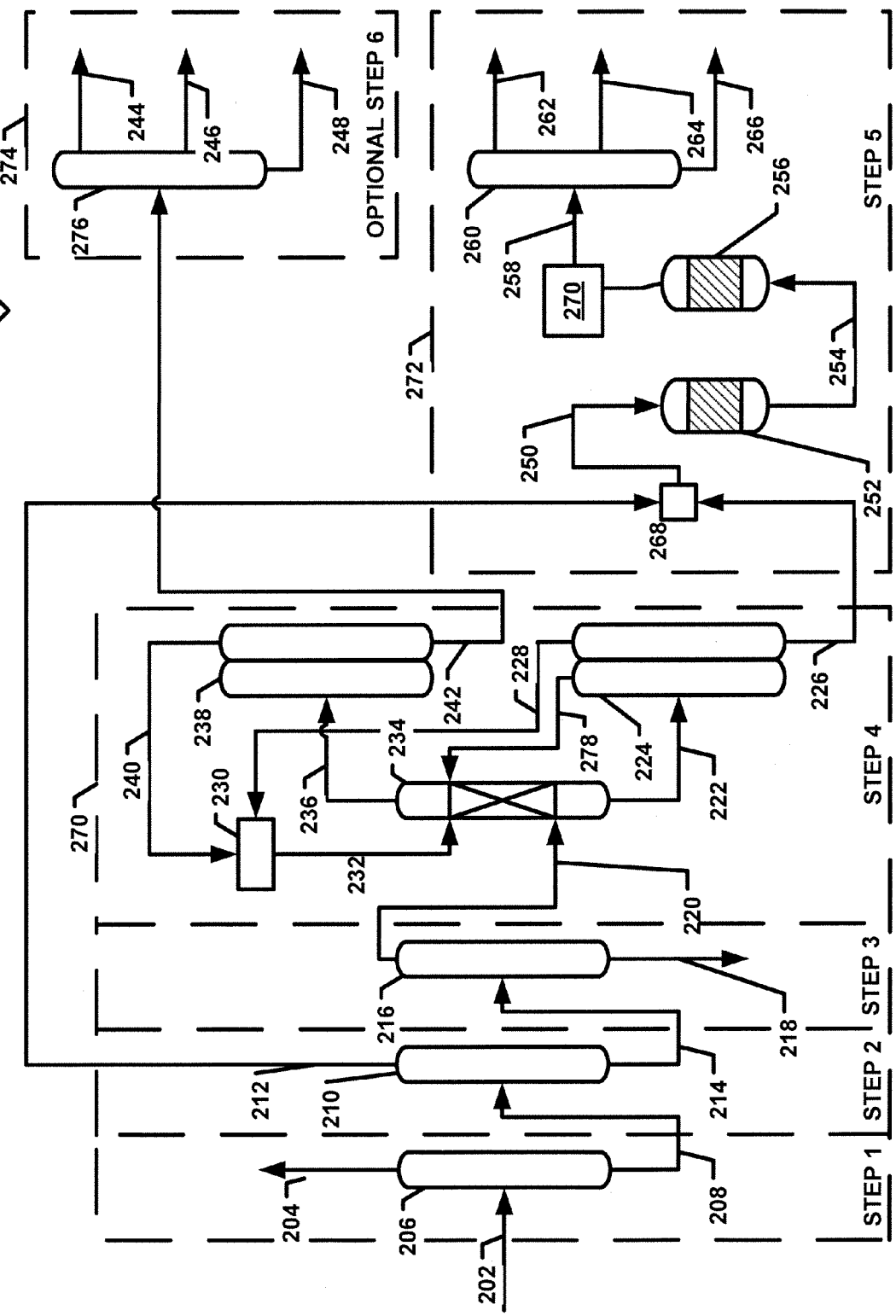
FIG. 2 is a diagram of a system for processing waste oil in accordance with an exemplary embodiment of the present disclosure.

FIG. 2 is a diagram of a system 200 for processing waste oil in accordance with an exemplary embodiment of the present disclosure. In step 1, the feedstock is heated and charged into a distillation system 206. In distillation system 206, a light oil fraction, namely materials that have a boiling point less than approximately 350° F., line 204, is separated from the oil feedstock, line 202, thereby producing a de-volatized oil fraction, line 208. The distillation system 206 consists of one or more vessels which may be operated under vacuum, at atmospheric conditions or at pressure and can be single or multiple staged, as known to those skilled in the art. One or more of the vessels may be designed to enable an average residence time for the de-volatized oil of between 5 minutes and 5 hours and generally around 1 hour. The light oil fraction, line 204, generally consists of one or more low boiling point contaminants such as water, light hydrocarbons, glycols, solvents and other volatile materials such as might be found to have been combined with the oil feedstock. The low boiling point contaminants may also contain breakdown products from service. In certain rigorous applications, it is possible for the oil molecules, or, if present, performance enhancing chemicals to split into two or more smaller molecules. One or more of these may be volatile below 350° F. and would end up in the light oil fraction, line 204. In the instances where the feedstock has not split or been contaminated with volatile materials, the flow of the light oil fraction, line 204, may be minimal or zero.

The de-volatized fraction, line 208, consists of the material that generally has a boiling point greater than 350° F. This stream discharges from the bottom of distillation system 206 and is optionally heated and charged into a second distillation system 210. The second distillation system 210 consists of one or more distillation devices such as columns, evaporators or the like known to those skilled in the art, for fractionating streams based on boil point. The distillation devices may be operated under vacuum, at atmospheric conditions or at pressure and can be single or multiple staged as known to those skilled in the art. One or more of the vessels may be designed to enable an average residence time for the de-volatized oil of between 5 minutes and 5 hours and generally around 1 hour. In distillation system 210, at least a portion of the molecules having a boiling point between approximately 350 and 650° F., the fuel oil fraction, are separated from the balance of the de-volatized stream, line 208, to form a heavy oil fraction. The fuel oil fraction, line 212, passes from the distillation devices whereon it is condensed and fed to the hydration system feed accumulator, device 268. The heavy oil fraction consisting of material with a boiling point greater than 650° F. is passed via line 214 to the third step. Optionally, this stage of the process can be broken up into two or more steps which further separate the oil into two or more fractions. For example, two distillation steps each consisting of one or more vessels can be used to separate the oil into a first 350 to 500° F. fraction, a second 500 to 650° F. fraction and a heavy oil fraction. One or both of the first 350 to 500° F. fraction or the second 500 to 650° F. fraction can then be fed via line 212 to hydration system feed accumulator 268.

In the third step, the heavy oil, line 214, is further heated and passed to distillation system 216 wherein oil with a boiling point of approximately 650 and 1,200° F. is separated from the balance of the heavy oil stream creating a partially purified oil stream, line 220, and a residual stream, line 218. The third distillation system 216 consists of one more columns, evaporators or other suitable distillation devices for fractionating streams based on boil point. Third distillation system 216 has a design that optimizes the distillation at lower temperatures, to avoid the cracking and fouling of the oil, by utilizing the inverse relationship between vacuum and temperature. In general, as you lower the amount of vacuum, the temperature required to produde the same distillation profile also decreases, and as pressure increases, higher temperatures are required to get the same distillate. With no vacuum or increased pressure, the boiling temperature is high, whereas with vacuum, the boiling temperature will drop. The columns of third distillation system 216 are designed to facilitate a low vacuum, such as one having 20 mm of mercury or less. This design can utilize an unpacked column, a single stage with little bits of grit to limit entrainment, and a horizontal section a series of chevrons on a series of circles, to provide a steeper vacuum at the flash zone. The distillation devices may be single or multiples staged and operated under vacuum, at atmospheric conditions or at pressure and can be single or multiple staged, or other suitable systems or devices. One or more of the vessels may be designed to enable an average residence time for the de-volatized oil in excess of 5 minutes. The material having a boiling point less than 1200° F. (partially purified oil) passes from the distillation device 216, whereon it is condensed, collected and passed through line 220 to step 4 of the process. The residual is cooled to 350° F. and passed to storage where it will be sold as a petroleum product.

The fourth step of the process consists of liquid/liquid extraction and recovery. The partially purified oil, line 220, is generally passed through a cooler where it is cooled to between 100 and 300° F. and into a liquid/liquid extraction system 270. In the liquid extraction system, an extractant is used to preferentially remove certain molecular types from the partially purified oil. The liquid/liquid extraction system may consist of one or more contacting vessels 234 which may be single or multiple staged and are designed to induce contact between the partially purified oil and the extractant. The contacting vessel(s) 234 is shown with a top and a bottom. A contact section is shown schematically in the center portion of the vessel 234. A liquid extractant accumulation and storage vessel is shown at 230 and supplies the liquid extractant to an upper portion of vessel 234 near its top via a line 232. The extractant moves downwardly, counter-current to the flow of the partially purified oil stream via a line 220, which is introduced near the bottom of the contact section. Upon contact, the extractant attracts, and weakly bonds to, the molecules that are polar, aromatic, olefinic or unsaturated in nature, drawing them downward to the bottom of the column (the extract), thereby extracting them from the partially purified oil, creating a more purified, saturated, paraffinic oil stream (the raffinate).

The raffinate stream consisting of purified oil fraction with a portion of the extractant is recovered from the top of vessel 234 and passed via a line 236 to an extract recovery system. The extractant recovery system consists of one or more vessels designed to recover and purify the extractant. In one embodiment, the purified oil/extractant stream 236 is heated to between 350° F. and 650° F. and passed to two or more distillation vessels 238 having a too and a bottom, whereby the extractant is separated from the purified oil molecules with cross-current heat exchangers or other suitable energy recovery being employed to increase extractant recovery without significant increase in energy cost. The recovered extractant is provided to extractant accumulation vessel 230 and the purified oil, line 242, sent to storage. One or more of the vessels 238 can also be configured to fractionate the purified oil into different viscosity cuts. Optionally, a separate fractionation column 276 can be used whereby the purified oil is fractionated by distillation into different viscosity cuts. The distillation vessels 238 can be operated under vacuum, at atmospheric conditions or under pressure and may have single or multiple stages. Additionally, steam or other gaseous streams can be used to influence partial pressure and help separate the extractant from the purified oil. The extractant is recovered through a line 240, and is typically treated to remove water, low boiling point contaminants and the like, and neutralize organic acids, as known to those skilled in the art, and returned to extractant accumulator 230.

A bottom extract stream 222 is also recovered from vessel 234 and passed to a second extractant separation system 224 having a plurality of columns, each having a top and a bottom. The use of multiple columns increases the efficiency of extractant separation, with a small increase in energy costs through the use of energy recovery, such as cross-current heat exchangers. In the second extractant separation system 224, the extractant is separated from the extracted molecules (contaminant fraction) and passed via a line 228 to the extractant accumulator 230. The contaminant fraction is recovered from the bottom of vessel 224 and is passed via a line 226 to the feed accumulator for the hydrogenation system 268. The second extractant recovery system consists of two or more vessels designed to recover and purify the extractant from the extract (contaminant) oil. In one embodiment, the purified oil/extractant stream 222 is heated to between 350° F. and 650° F. and passed to one or more distillation vessels 224, each having a top and a bottom, whereby the extractant is separated from the contaminant oil molecules with the extractant being distilled, condensed and then recovered in a first line 278 back to vessel 234 and in a second line 228 to the extractant accumulation vessel 230. The use of the first line 278 increases process efficiency by providing additional solvent to vessel 234 that has not been subjected to additional processing. The distillation vessels 224 can be operated under vacuum, at atmospheric conditions or under pressure and may have single or multiple stages. Additionally, steam or other gaseous streams can be used to influence partial pressure and help separate the extractant from the contaminant oil. The extractant is recovered through a line 228, and is typically treated to remove water, low boiling point contaminants and the like, and neutralize organic acids, as known to those skilled in the art, and returned to extractant accumulator 230.

In the hydrogenation section 272, the material in the hydrogenation feed accumulator is heated and passed to the first treatment zone 252 in the hydrogenation system 272. Hydrogen is heated and added to stream 250. The stream is then passed through a third heater and into zone 252. Zone 252 consists of one or more guard beds designed to remove catalyst poisons in the oil that might otherwise poison the hydrotreating catalyst. These vessels have a top and bottom and include a contact zone containing a catalyst, spent catalyst, activated clay, or the like, as known to those skilled in the art. It will be understood that hydrogen could be injected into line 250 at a plurality of points or into vessels in zone 252 at a plurality of points. The product from the vessels in zone 252 is recovered through a line 254 and passed to a hydrogenation reactor zone 256.

Generally, the vessels in zone 256 have a top and a bottom and include a catalytic bed. Hydrogen may be added at various points along line 254 or at various points along the length of the vessels in zone 256. To some extent, unsaturates including olefins, aromatics and molecules containing contaminants such as sulfur, nitrogen, oxygen, heteroatoms, and the like, are hydrogenated in zone 256. In one exemplary embodiment, zone 256 can include a reactor with catalyst, where hydrogen and oil ager generated. Line 258 can include hydrogen separation and recovery system 270 to remove this hydrogen. In addition, zone 256 can be implemented as two or more vessels, which can be run in series or parallel. A series combination can be used to obtain a better quality product, such as by using intermediate separation in different vessels, such as to treat for sulphur removal, napthenics removal, or removal of other compounds. Zone 256 can also be used to form more saturated hydrocarbon molecules and volatile compounds of hydrogen. The contaminated oil, which has now been upgraded through hydrogen saturation forming a saturated oil product, is recovered through a line 258 and passed to a fractionation column 260. In the fractionation column 260, the saturated oil is fractionated in one or more of naphtha, diesel oil and base oil.

In the embodiment described above in steps 1, 2 and 3, one distillation column is typically used for each step. Steps 1 and 2 are preferably undertaken at atmospheric pressure, whereas step 3 is undertaken at a vacuum generally between 2 to 200 mmHg. Furthermore, in general, the residence time is increased by designing the vessels with an enlarged lower column section in which the non-volatile fraction is held before being passed to the next step. Alternatively, a second holding vessel which is closely associated with the distillation column of each step could be used. In the practice of this invention, it may be desirable to use as few as one or as many six distillation systems to undertake steps 1 through 3.

In all of the steps described in the embodiment above where a distillation system is envisioned, vessels are used to separate various constituents from each other. These vessels include any suitable vessel or system that effects a single or multiple stages of separation including simple evaporators, thin or wiped film evaporators, columns, packed columns, vessels, tanks, pipes or other suitable systems or devices. These vessels may be operated under vacuum, at atmospheric pressure or elevated pressure.

In the embodiment described above, prior to the first vessel of step 1, an optional treatment vessel can be used to chemically treat the composite stream prior to entry into distillation system 206 to facilitate treatment. This chemical treatment can be an alkali or base material such as sodium carbonate, sodium bicarbonate, sodium hydroxide, potassium hydroxide, or an acid such as sulfuric acid or other chemicals known to reduce the tendency to foul, enhance separation, processability, equipment availability, or the like, or to enhance the quality of the synthetic oil or other products, as known to those skilled in the art.

In the practice of the present invention, it may be desirable in some instances for the boiling point of stream 212 to be generally between 350° F. and 500° F., thereby enriching line 214 with material with a boiling point between around 500° F. and 650° F.

In some instances, it may be preferable to create more than one partially purified oil stream from distillation system 216, whereby the partially purified oil streams are distinguished in terms of distillation profile. In this instance, one or more storage vessels can be used between step 3 and step 4 to temporarily store partially purified fractions and one partially purified fraction at a time can be passed to step 4 on a blocked out basis. Thus, step 4 would be used to purify each of the partially purified oil fractions individually. While one first partially purified synthetic oil stream is being processed through step 4, the other stream(s) are accumulated in intermediate storage tanks. When the first stream intermediate storage tank is close to being emptied, the feed to step 4 can be switched to process the content of a second intermediate storage tank containing a second partially purified oil stream.

In the embodiment shown above, the extractant recovered from the oil stream 240 and the contaminant stream 228 are consolidated in an extractant accumulator vessel 230. Either prior to vessel 234 or post vessel 238, the extractant can be treated to remove any contaminants such as water or similar boiling point materials that may have contaminated the extractant. Such treatments include distillation, extraction, absorption, adsorption, osmosis, chemical treatment or other suitable processes.

In the fourth step of the embodiment shown above, the extraction process used in vessel 234 may be a suitable process, such as extractant extraction, with materials such as ethanol, diacetone-alcohol, ethylene-glycol-mono(low alkyl) ether, di-ethylene-glycol, diethylene-glycolmono(low alkyl) ether, o-chlorophenol furfural, acetone, formic acid, 4-butyrolacetone, low-alkyl-ester of low mono- and dicarbonic acids, dimethylformamide, 2-pyrrolidone and N-(low alkyl)2-pyrrolidone, N-methyl-2-pyrolodone, epi-chlorohydrin, dioxane, morpholine, low-alkyl- and amino(low-alkyl) morpholine, benzcnitrile and di-(low-alkyl)sulfoxide, and phosphonate, or other suitable processes.

N-methyl-2-pyrolodone is a preferred extractant for step 4 of the process of the present invention. In one exemplary embodiment, extraction is undertaken at a temperature between about 100 and about 250° F. and preferably between about 130 and about 190° F. Typically, both the extractant and partially purified oil are fed into the extraction column within this temperature range although not necessarily at the same temperature. The extractant dosage (percent of extractant relative to feed) fed to the extraction column is typically between 50 and 1000% by volume and preferably between 100 and 400%. Typically, extraction is undertaken in a packed or trayed column whereby the extractant is fed into the top of the column and partially purified synthetic oil is fed into the bottom. The packed column can contain structured packing, random packing or other suitable packing. Water may be injected into the extractant or extraction column as desired to control extractant selectivity. Similarly, temperature gradients or regional heating or cooling can be used at various points along or across the extraction column to affect performance and selectivity. Recycles of both raffinate and extract at similar or different temperatures can also be employed. In some instances, it may be beneficial to remove a side stream from the extraction column, raffinate or extract streams cool, and separate a portion of the extractant from the oil and return the oil to the column. The extractant may be recovered from the raffinate stream in line and the extract stream in line using distillation. The distillation can be undertaken atmospherically or by using vacuum. Flash separators or multi-stage columns can be used or combinations thereof can be used in order to separate the extractant from the synthetic or the extracted contaminants.

In the exemplary embodiment described above, additional processing may be undertaken on the distillate stream, line 204, from system 206 such as further separating the constituents of this stream such as water, glycols, extractants, light hydrocarbons and the like, thereby creating separate products which may be used or further upgraded to higher quality products. In the disclosed embodiment, only one distillate cut is taken from distillation system 206.

A phase transfer catalyst or the like can also or alternatively be used to enhance the operation of the fourth step of the process, whereby the efficiency, selectivity and the like of the process are enhanced, thereby providing for better separation of the high quality base oil molecules from the lower quality molecules.

In the embodiment described above, flash vessels are used to separate various constituents in steps 1, 2 and 3. These vessels include any vessel or system that effects a single stage of separation including simple evaporators, thin or wiped film evaporators, columns, vessels, tanks, pipes, and the like, as known to those skilled in the art. The flash vessels are also designed to provide for a residence time from 5 minutes to 5 hours and generally around 60 minutes. This residence time is generally enabled through the use of a liquid well either at the bottom of or otherwise associated with the vessel.

In the embodiment described above, stage four is used to separate the contaminant from the purified oil molecules, thereby creating a first purified oil stream wherein the concentration of aromatics, polars, unsaturates, heteroatoms, and the like, is lower than the second stream and thereby consists of higher quality base oil. It is also possible to further upgrade this purified oil stream using processes similar to those described in step 5 by converting a portion of any remaining aromatic, polar, unsaturated, heteroatom molecules and the like, to higher quality molecules, thereby further purifying it, increasing the degree of saturation and thereby producing an highly purified oil. This oil may be suitable for use as a white oil in the medicinal or food processing industries as well as a lubricating oil in the industrial lubrication markets.

In the embodiment shown above, the extractant recovered from lines 228 and 240 of step 4 is combined in the extractant accumulation unit 230. In the extractant accumulation unit 230, the extractant may be purified by removing water and other low boiling point contaminants prior to re-use. The extractant can also be treated at this stage with bases and the like, as known to those skilled in the art, to neutralize organic acids that may have built up in the extractant.

In the embodiment described above, distillation systems 206 and 210 are operated at atmospheric pressure. These vessels could also be operated at pressure or under vacuum by varying temperature, as known to those skilled in the art, to effect similar separation of the oil fractions from the feedstock.

The product stream recovered through line 218 typically comprises asphalt flux range materials and includes heavy oils, polymer, salts, solids, other high boiling range materials and the like, which are constituents of the feedstock stream 202. The residual stream recovered from this system 216 is generally cooled to approximately 350° F. and passed to heated storage.

In the preferred embodiment of the present invention as discussed above, hydrofinishing is used to purify and saturate the contaminant and/or fuel fractions (lines 226 and 212, respectively, collectively the unsaturated oil stream) as a final step. The unsaturated oil stream is mixed with 50 to 2000 scf of hydrogen per barrel of base oil feed, preferably between 70 and 150 scf of hydrogen per barrel of base oil feed, heated to between about 500 and about 1200° F., preferably between about 650 and about 850° F. and pressurized to between about 100 and about 3000 psig and preferably between about 500 and about 1500 psig. The mixture is passed through a guard bed consisting of activated clay or spent catalyst and then through a reactor containing one or more hydrogenation catalysts with metal components from Groups V(b), VI(b) and VIII of the Periodic Table or other suitable materials. Preferable compounds are nickel, molybdenum, vanadium, tungsten or cobalt metal supported on carriers such as activated carbon, kieselguhr, silica, alumina, and the like, such as a cobalt-molybdenum on alumina, nickel-molybdenum on alumina or nickel-tungsten on silica/alumina. Typically, the hydrogenation is undertaken at a space velocity of about 0.1 to about 10 and preferably between 0.5 and 2 volumes of liquid feed per volume of catalyst per hour. Typically, only one reactor stage is used. However, several stages can be used if desired by using multiple reactors in a series. After the hydrogenation treatment, the base oil fraction is separated from the hydrogen gas and volatile reaction products in a flash vessel, which may be operated at reduced pressure. Typically, the pressure is between a full vacuum and about 100 psig, although wide variations in the suitable pressure are possible.

In the fifth stage of the process presented in this embodiment, it may be advantageous to have multiple guard beds, run reactors in parallel or series to utilize phase or separation the like between reactors or between guard beds and reactors. Furthermore, in some instances it may be advantageous to strip the saturated oil of light contaminants or further fractionate it into different cuts. Although the system described herein does not specify a hydrogen recovery system, one could be employed to recover and purify un-reacted hydrogen and reaction products after recovery separation from the product base oil.

The disclosed embodiment shows continuous flow between the steps of the operations. It may be desirable in certain instances to have intermediate storage vessels between the steps to allow for process surges, contain off specification material, smooth operations, quality control, allow for more than one cut of base oil distillate, and the like. Many variations and schemes are possible to incorporate regenerative or recuperative heat exchangers to recover heat from process streams and optimize the thermal efficiency of the process.

By the process of the present invention, the oil feedstock is separated into a number of fractions in the first three steps. In the fourth step, the one fraction produced in step 3 is further refined using liquid/liquid extraction to produce a base oil fraction suitable for the manufacture of ILSAC GF5. The extract from the fourth step is combined with the fuel oil fraction from step 2 and purified through hydrogenation to produce a saturated fraction which is subsequently fractionated to produce a high quality base oil and one or more fuel fractions at least one of which is suitable for use as an on-road low sulfur fuel in diesel engines. The combination of these steps has produced a surprisingly superior process that yields a surprisingly high yield of base oil suitable for use in the manufacture lubricants for modern high tech, environmentally friendly engines, high quantity fuel products and the full recovery of all petroleum fractions found in the feedstock.

The use of this five step process provides several significant advantages over existing process methodologies. The present invention enables both objectives of manufacturing products that meet the demands of the market for higher quality, environmentally friendly products and the desire to maximize the amount of base oil produced from feedstock. Existing processes can only produce lower quality base oils and fuels and are not able to produce the same yield or product slate as the method of this invention.

The total base oil produced through lines 262, 264 and 266 is more than has been produced by previous processes and is of higher overall quality. Stream 242 is capable of being used in the production of lubricants that meet GF5 standards that are thought to be as well positioned to meet new standards as they arise. When previous extraction processes are used to separate the base oil from other undesirable components, the extraction treatment is required to be relatively severe in order to produce high quality base oil and consequently results in a base oil yield loss due to over extraction. Similarly, when previous hydrotreating processes are used, relatively severe treatment is again required in order to produce high quality base oil. This severe treatment results in cracking of some of the base oil molecules into smaller non-base oil molecules, resulting in yield loss. Thus, neither of these processes alone is capable of producing a high yield and high quality base oil.

According to the present invention, heavy oil material charged to extraction and severe extraction can be used to separate the polar, aromatic and unsaturated oil molecules from the paraffinic, saturated high quality molecules since the extracted oil is recovered and upgraded in the next stage without concern for yield loss. The base oil is recovered in relatively high yield quantities, typically from about 75 to about 95% of the oil content of the feedstock to the extraction system 234, depending on the desired quality of base oil. Further, the contaminated oil removed in the extraction process, which includes contaminants of various types, is recovered through line 226 and passed to upgrading where it is upgraded to on-road diesel fuel and saturated base oil. Typically, from about 10 to about 30% of the base oil contained in the feedstock stream 202 is recovered through line 258, again depending on quality.

The combination of these steps results in a much larger recovery than is typically achieved by any known process. For instance, the use of hydrogenation to upgrade the entire base oil stream results in cracking a large number of molecules which would otherwise be suitable as base oil. Others may be isomerized or otherwise modified over the cracking catalyst. The process enables the recovery of over 90% of the base oil available in the feedstock 202.

Another unexpected advantage of the current disclosure over existing technologies is its ability to process oils recovered from combustion engine services of varying specification and quality and still produce high quality products. Existing processes are highly influenced by feedstock quality and their product quality and/or yield are highly influenced by feedstock quality. The present disclosure is capable of processing a wide variety of feedstocks and still manufacture high quality products and maintain a high yield of total base oil product.

The present disclosure also has the unexpected benefit of reducing capital expenditures. In most processes, the good base oil molecules are treated with the contaminated base oil molecules even though upgrading of the good base oil molecules may not be necessary. Because of this, the process must be sized larger to process all of the base oil molecules together. In the current disclosure, the good base oil molecules are separated from the contaminated base oil molecules prior to upgrading the contaminated molecules. By doing so, the processing equipment can be sized to treat a much smaller stream thereby saving capital cost for expensive high pressure and high temperature upgrading equipment. The cost of upgrading is also reduced due to the lower operating cost associated with processing the stream wherein the contaminates have been concentrated.

The use of the type of distillation system outlined herein is considered to provide substantial advantages over previous systems. The process provides additional efficiency and economic benefits since it uses simple distillation vessels enabling more effective separation with less complicated equipment at each step. Similarly, it enables excellent separation of the physical contaminants typically found in oils recovered from combustion engine service yielding distillates suitable for further processing and upgrading. The sequential removal of physical contaminants also enables good control over product streams and unit operations availability. Columns that do not have mechanical means, such as those found in film evaporators and the like, result in lower capital and operating costs. Similarly, simple distillation columns avoid the typical problem packing fouling, which can be experienced when processing used oil.

A surprising benefit of the process is its ability to avoid the problem of heat exchanger and equipment fouling typically experienced in processing oils recovered from combustion engine service. The design of the vessels with increased residence time enables certain contaminants in the feedstock sufficient time to decompose, thereby stabilizing the oil streams and reducing fouling. Finally, the present disclosure enables the production of both high quality base oils and one-road diesel fuel. No other re-refining technology heretofore has been able to do this. While the present invention has been described by reference to certain of its preferred embodiments, it is pointed out that the embodiments described are illustrative rather than limiting in nature and that many variations and modifications are possible within the scope of the present invention. Many such variations and modifications may be considered obvious and desirable by those skilled in the art based upon a review of the foregoing description of preferred embodiments.

Figure 3:
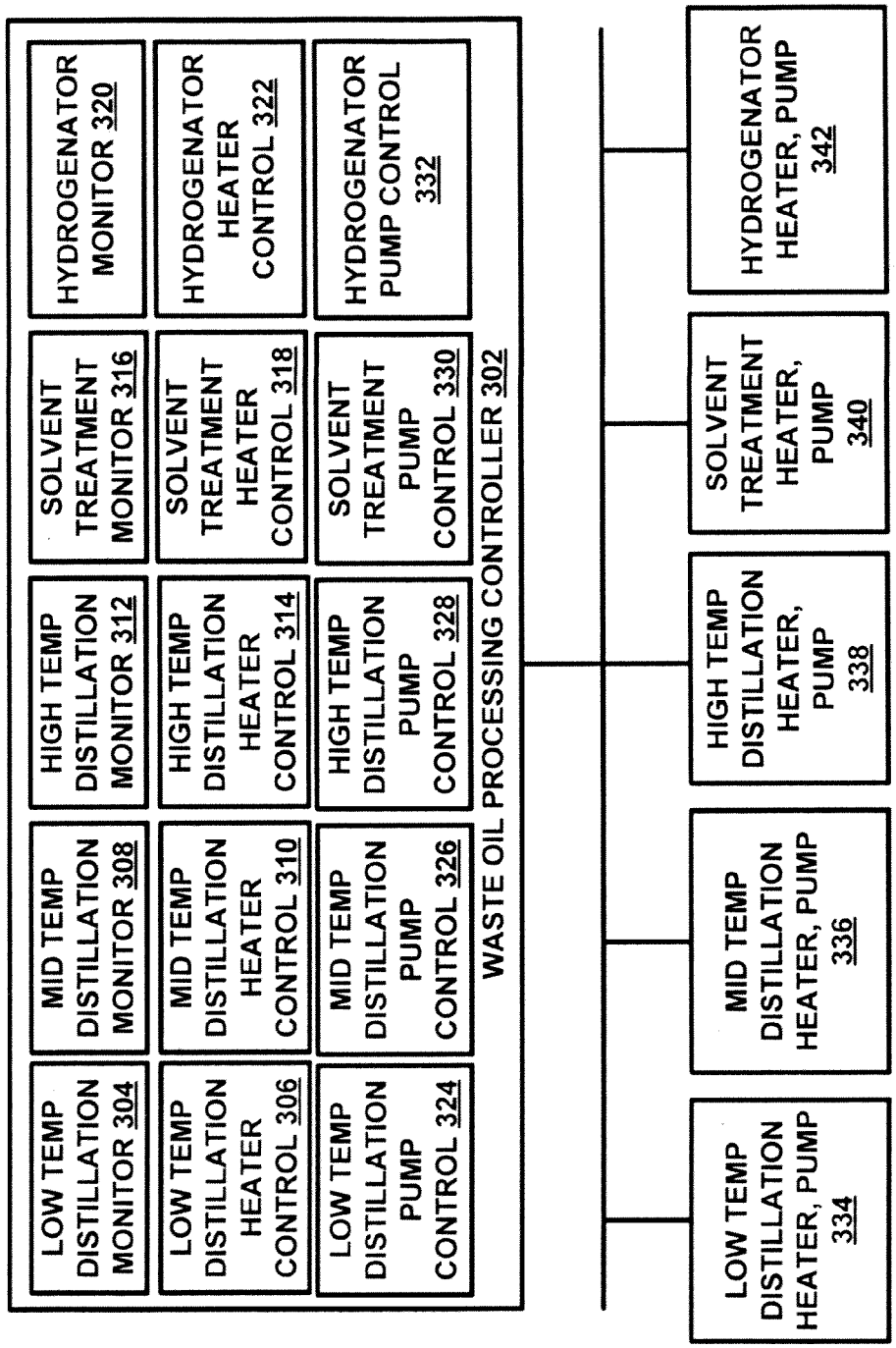
FIG. 3 is a diagram of a controller for controlling waste oil processing in accordance with an exemplary embodiment of the present disclosure.

FIG. 3 is a diagram of a controller 300 for controlling waste oil processing in accordance with an exemplary embodiment of the present disclosure. Controller 300 can be implemented in hardware or a suitable combination of hardware and software, and can include one or more software systems operating on a processor. Controller 300 can also be used to implement offsite monitoring, for archiving of operations data (temperatures, pressures, recovered compounds) and subsequent statistical analysis of the archived operations data, to develop trends, to notify operators of maintenance requirements, to avoid shutdowns, to improve online reliability, to provide operator notices (e.g. trend of dropping temperatures, trend of increasing pressures) or for other suitable purposes.

As used herein, "hardware" can include a combination of discrete components, an integrated circuit, an application-specific integrated circuit, a field programmable gate array, or other suitable hardware. As used herein, "software" can include one or more objects, agents, threads, lines of code, subroutines, separate software applications, two or more lines of code or other suitable software structures operating in two or more software applications, on one or more processors (where a processor includes a microcomputer or other suitable controller, memory devices, input-output devices, displays, data input devices such as keyboards or mice, peripherals such as printers and speakers, associated drivers, control cards, power sources, network devices, docking station devices, or other suitable devices operating under control of software systems in conjunction with the processor or other devices), or other suitable software structures. In one exemplary embodiment, software can include one or more lines of code or other suitable software structures operating in a general purpose software application, such as an operating system, and one or more lines of code or other suitable software structures operating in a specific purpose software application. As used herein, the term "couple" and its cognate terms, such as "couples" and "coupled," can include a physical connection (such as a copper conductor), a virtual connection (such as through randomly assigned memory locations of a data memory device), a logical connection (such as through logical gates of a semiconducting device), other suitable connections, or a suitable combination of such connections.

System 300 includes waste oil processing controller 302, which includes low temperature distillation monitor 304, mid temperature distillation monitor 308, high temperature distillation monitor 312, solvent treatment monitor 316, hydrogenator monitor 320, low temperature distillation heater controller 306, mid temperature distillation heater controller 310, high temperature distillation heater controller 314, solvent treatment heater controller 318, hydrogenator heater controller 322, low temperature distillation pump controller 324, mid temperature pump control 326, high temperature distillation pump controller 328, solvent treatment pump controller 330 and hydrogenator pump controller 332 each of which can be implemented as one or more objects having associated graphical and functional characteristics. Consolidation of these monitors and controls in a single location, display panel or set of display panels allows process variables to be readily monitored and coordinated, unlike separate systems in different locations that have to be monitored and adjusted over time. Such separate systems can have process variations that are not observed by a single operator, which can result in lower quality, lower efficiency or other problems. These problems are more pronounced and significant when processing waste oil with high amounts of synthetic oil compounds, because the quality of the waste oil and the composite compounds of the waste oil can be highly variable, which can make it difficult to adjust process variables over time.

Low temperature distillation monitor 304 generates one or more low temperature distillation metrics, such as temperature, pump speed, pressure, flow rate or other suitable metrics. In one exemplary embodiment, low temperature distillation monitor 304 can include one or more user-selectable controls that allow a user to display or hide a metric, to increase the size of a display for a metric, to add an audible alarm for a metric, or other suitable functions.

Mid temperature distillation monitor 308 generates one or more mid temperature distillation metrics, such as temperature, pump speed, pressure, flow rate or other suitable metrics. In one exemplary embodiment, mid temperature distillation monitor 308 can include one or more user-selectable controls that allow a user to display or hide a metric, to increase the size of a display for a metric, to add an audible alarm for a metric, or other suitable functions.

High temperature distillation monitor 312 generates one or more high temperature distillation metrics, such as temperature, pump speed, pressure, flow rate or other suitable metrics. In one exemplary embodiment, high temperature distillation monitor 312 can include one or more user-selectable controls that allow a user to display or hide a metric, to increase the size of a display for a metric, to add an audible alarm for a metric, or other suitable functions.

Solvent treatment monitor 316 generates one or more solvent treatment system metrics, such as pump speed, pressure, flow rate or other suitable metrics. In one exemplary embodiment, solvent treatment monitor 316 can include one or more user-selectable controls that allow a user to display or hide a metric, to increase the size of a display for a metric, to add an audible alarm for a metric, or other suitable functions.

Hydrogenator monitor 320 generates one or more hydrogenator metrics, such as temperature, pump speed, pressure, flow rate or other suitable metrics. In one exemplary embodiment, hydrogenator monitor 320 can include one or more user-selectable controls that allow a user to display or hide a metric, to increase the size of a display for a metric, to add an audible alarm for a metric, or other suitable functions.

Low temperature distillation heater controller 306 generates one or more user-selectable controls for low temperature distillation heater and pump 334, such as an increase temperature control, a decrease temperature control or other suitable controls. In one exemplary embodiment, low temperature distillation heater controller 306 can interface with low temperature distillation monitor 304 to perform a suitable function in response to an alarm or setting, such as to increase a temperature in response to a low temperature alarm or setting, to decrease a temperature in response to a high temperature alarm or setting, or to perform other suitable functions.

Mid temperature distillation heater controller 310 generates one or more user-selectable controls for mid temperature distillation heater and pump 336, such as an increase temperature control, a decrease temperature control or other suitable controls. In one exemplary embodiment, mid temperature distillation heater controller 310 can interface with mid temperature distillation monitor 308 to perform a suitable function in response to an alarm or setting, such as to increase a temperature in response to a low temperature alarm or setting, to decrease a temperature in response to a high temperature alarm or setting, or to perform other suitable functions.

High temperature distillation heater controller 314 generates one or more user-selectable controls for high temperature distillation heater and pump 338, such as an increase temperature control, a decrease temperature control or other suitable controls. In one exemplary embodiment, high temperature distillation heater controller 314 can interface with high temperature distillation monitor 312 to perform a suitable function in response to an alarm or setting, such as to increase a temperature in response to a low temperature alarm or setting, to decrease a temperature in response to a high temperature alarm or setting, or to perform other suitable functions.

Solvent treatment heater controller 318 generates one or more user-selectable controls for solvent treatment valve and pump 340 such as an increase temperature control, a decrease temperature control or other suitable controls. In one exemplary embodiment, solvent treatment heater controller 318 can interface with solvent treatment monitor 316 to perform a suitable function in response to an alarm or setting, such as to increase a temperature in response to a low temperature alarm or setting, to decrease a temperature in response to a high temperature alarm or setting, or to perform other suitable functions.

Hydrogenator heater controller 322 generates one or more user-selectable controls for hydrogenator heater and pump 342, such as an increase temperature control, a decrease temperature control or other suitable controls. In one exemplary embodiment, hydrogenator heater controller 322 can interface with hydrogenator monitor 320 to perform a suitable function in response to an alarm or setting, such as to increase a temperature in response to a low temperature alarm or setting, to decrease a temperature in response to a high temperature alarm or setting, or to perform other suitable functions.

Low temperature distillation pump controller 324 generates one or more user-selectable controls for low temperature distillation heater and pump 334, such as an increase pump speed control, a decrease pump speed control or other suitable controls. In one exemplary embodiment, low temperature distillation pump controller 324 can interface with low temperature distillation monitor 304 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Mid temperature distillation pump controller 326 generates one or more user-selectable controls mid temperature distillation heater and pump 336, such as an increase pump speed control, a decrease pump speed control or other suitable controls. In one exemplary embodiment, mid temperature distillation pump controller 326 can interface with mid temperature distillation monitor 308 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

High temperature distillation pump controller 328 generates one or more user-selectable controls for high temperature distillation heater and pump 338, such as an increase pump speed control, a decrease pump speed control or other suitable controls. In one exemplary embodiment, high temperature distillation pump controller 328 can interface with high temperature distillation monitor 312 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Solvent treatment pump controller 330 generates one or more user-selectable controls for solvent treatment heater and pump 340, such as an increase pump speed control, a decrease pump speed control or other suitable controls. In one exemplary embodiment, solvent treatment pump controller 330 can interface with solvent treatment monitor 316 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Hydrogenator pump controller 332 generates one or more user-selectable controls for hydrogenator heater and pump 342, such as an increase pump speed control, a decrease pump speed control or other suitable controls. In one exemplary embodiment, hydrogenator pump controller 332 can interface with hydrogenator monitor 320 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Low temperature distillation heater and pump 334 can include one or more heaters, pumps, valves, chillers, compressors and other associated components of a low temperature distillation apparatus such as distillation 206. Although exemplary systems for heater and pump control are described herein, additional systems for individual or group control of valves, chillers, compressors or other components can also or alternatively be provided.

Mid temperature distillation heater and pump 336 can include one or more heaters, pumps, valves, chillers, compressors and other associated components of a low temperature distillation apparatus such as distillation 210. Although exemplary systems for heater and pump control are described herein, additional systems for individual or group control of valves, chillers, compressors or other components can also or alternatively provided.

High temperature distillation heater and pump 338 can include one or more heaters, pumps, valves, chillers, compressors and other associated components of a high temperature distillation apparatus such as distillation 216. Although exemplary systems for heater and pump control are described herein, additional systems for individual or group control of valves, chillers, compressors or other components can also or alternatively be provided.

Solvent treatment heater and pump 340 can include one or more heaters, pumps, valves, chillers, compressors and other associated components of a solvent treatment apparatus such as 234. Although exemplary systems for heater and pump control are described herein, additional systems for individual or group control of valves, chillers, compressors or other components can also or alternatively be provided.

Hydrogenator heater and pump 342 can include one or more heaters, pumps, valves, chillers, compressors and other associated components of a synthetic separator apparatus such as hydrogenator 272. Although exemplary systems for heater and pump control are described herein, additional systems for individual or group control of valves, chillers, compressors or other components can also or alternatively be provided.

Figure 4:
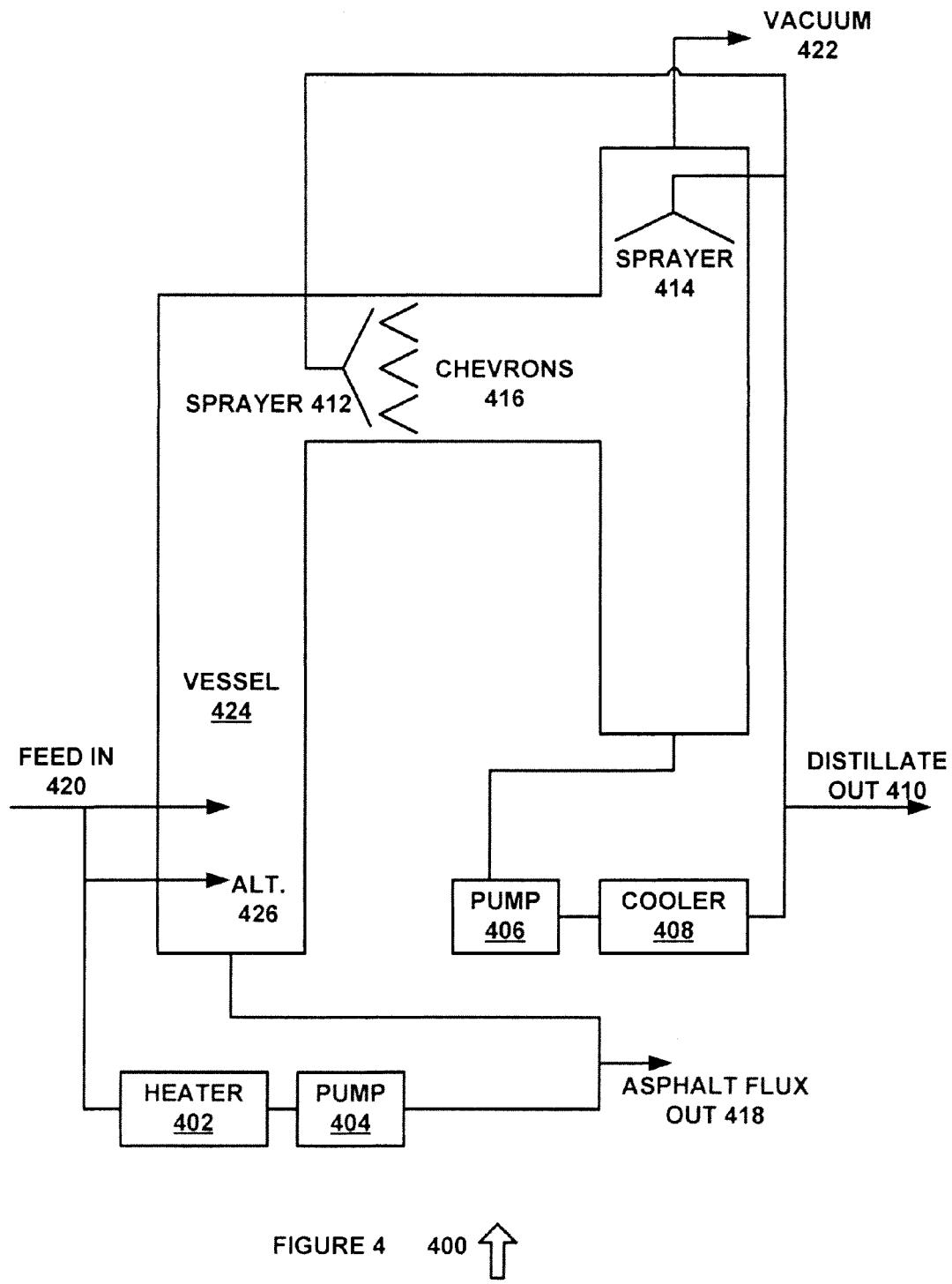
FIG. 4 is a diagram of a distillation column in accordance with an exemplary embodiment of the present disclosure.

FIG. 4 is a diagram of a distillation column 400 in accordance with an exemplary embodiment of the present disclosure. Distillation column 400 can be used for separation of components with a boiling point of greater than 1200° F. at atmospheric pressure, such as in step 3 of systems 100 or 200, or for other suitable purposes.

Distillation column 400 includes feed in 420, which provides a suitable feedstock to vessel 424. Distillation occurs in vessel 424 for components having a normal boiling point 1200° F. or greater at atmospheric pressure, but the operating temperature of vessel 424 can be reduced by vacuum 422, which decreases the ambient pressure within vessel 424 to reduce the effective boiling point, and to prevent cracking and fouling of the feedstock and other suitable purposes. In order to remove asphalt and other remnants from the residue in this stage of the process, pump 404 can be used to extract the residue, and asphalt flux 418 is extracted from the residue before the liquid portion of the residue is circulated through heater 402 by pump 404 and inserted back into feed input 420 or alternate input 426.

As the distillate rises through the first vertical section of vessel 424, it is sprayed with condensed distillate through sprayer 424 and condenses on chevrons 416 in a horizontal section of vessel 424. A second sprayer 414 is used to further recover distillate, which collects at the bottom of the second vertical section of vessel 424, where it is pumped out by pump 406, cooled through cooler 408 and removed through distillate out line 410. A portion of the cooled distillate is fed back into vessel 424 through sprayers 412 and 414, as described above.

In operation, distillation column 400 allows components having a boiling point of 1200° F. or greater at atmospheric pressure to be removed without cracking or fouling at a lower absolute temperature, by drawing a vacuum and using additional processing to reduce the operating pressure within vessel 424.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

What is claimed is:

1. A method for producing oils from waste oil, the method comprising:
   a) controlling separation of at least a portion of material having a boiling point less than about 350° F. from feedstock to produce a de-volatized oil fraction and a light oil fraction using a central controller and automatically in response to a first sensor setting;
   b) controlling separation of at least a portion of material with a boiling point greater than about 350° F. and less than about 650° F. from the de-volatized oil fraction to produce a fuel oil fraction and a heavy oil fraction using the central controller and automatically in response to a second sensor setting;

c) controlling separation of at least a portion of material with a boiling point greater than about 1200° F. from the heavy oil fraction to produce a partially purified oil fraction and a residual fraction using the central controller and automatically in response to a third sensor setting;

d) controlling treatment of the partially purified oil fraction to separate the partially purified oil faction into a purified oil fraction and a contaminant fraction using liquid/liquid extraction with extractant recovery processing, using the central controller and automatically in response to a fourth sensor setting;

e) controlling hydrogenation of the contaminant fraction and the fuel oil fraction to remove predetermined compounds, further saturating the contaminant fraction and thereby creating a saturated oil fraction, using the central controller and automatically in response to a fifth sensor setting; and f) fractionating the saturated oil stream to produce one or more of a naphtha fraction, a diesel oil fraction and a base oil fraction;

wherein controlling the separation of the portion of material with the boiling point greater than about 1200° F. comprises spraying cooled distillate from a vessel back into the vessel at a predetermined location.

2. The method of claim 1, wherein the feedstock consists of oils that met at least one of American Petroleum Institute standards SJ/SL/SM/SN or higher or CG-4/CH-4/CI-4/CJ-4 or higher specifications when the feedstock was first put into service.

3. The method of claim 1 wherein a) further comprises automatically controlling a low temperature distillation heater and a low temperature distillation pump.

4. The method of claim 3 wherein b) further comprises automatically controlling a middle temperature distillation heater and a middle temperature distillation pump.

5. The method of claim 4 wherein c) further comprises automatically controlling a high temperature distillation heater and a high temperature distillation pump.

6. The method of claim 1 wherein the fuel oil fraction is separated from the heavy oil fraction by at least one of atmospheric or vacuum distillation.

7. The method of claim 5 wherein d) further comprises automatically controlling a solvent treatment heater and a solvent treatment pump.

8. The method of claim 7 wherein e) further comprises automatically controlling a hydrogenator heater and a hydrogenator distillation pump.

9. The method according to claim 1 whereby the recovered oil is treated with an alkali or base to condition the feedstock using a central controller.

10. The method according to claim 9 whereby the alkali or base is one of sodium carbonate, sodium hydroxide, and potassium hydroxide.

11. The method according to claim 1 whereby the recovered oil is treated to remove water and light hydrocarbons using a central controller.

12. The method of claim 1 wherein the purified oil fraction and the contaminant fraction are separated by at least one of filtration, ultrafiltration, molecular sieves, extraction, extractant extraction, absorption, and adsorption.

13. The method of claim 1 wherein the purified oil fraction and the contaminant fraction are separated by liquid/liquid extraction using a central controller.

14. The method of claim 13 wherein the liquid/liquid extraction is performed using one or more of ethanol, diacetone-alcohol, ethylene-glycol-mono(low alkyl) ether, di-ethylene-glycol, diethylene-glycolmono(low alkyl) ether, o-chlorophenol furfural, acetone, formic acid, 4-butyrolactone, low-alkyl-ester of low mono- and dicarbonic acids, dimethylformamide, 2-pyrrolidone and N-(low alkyl)2-pyrrolidone, N-methyl-2-pyrrolidone, epi-chlorohydrin, dioxane, morpholine, low-alkyl- and amino(low-alkyl)morpholine, benzonitrile and di-(low-alkyl)sulfoxide and phosphonate.

15. The method of claim 13 wherein the liquid/liquid extraction is performed using two or more of ethanol, diacetone-alcohol, ethylene-glycol-mono(low alkyl) ether, di-ethylene-glycol, diethylene-glycolmono(low alkyl) ether, o-chlorophenol furfural, acetone, formic acid, 4-butyrolactone, water, aqueous salts, low-alkyl-ester of low mono- and dicarbonic acids, dimethylformamide, 2-pyrrolidone and N-(low alkyl)2-pyrrolidone, N-methyl-2-pyrrolidone, mono or poly protic acids, mineral acids, carboxylic acids, hydroxide bases, carbonate bases, mineral bases, epi-chlorohydrin, dioxane, morpholine, low-alkyl- and amino(low alkyl)morpholine, benzonitrile and di-(low-alkyl)sulfoxide and phosphonate.

16. The method according to claim 12 wherein at least one of the liquids is the extractant N-methyl 2 pyrrolidone.

17. The method of claim 1 wherein the one or more of the oil fractions is suitable for use in ILSAC GF4 or higher applications.

18. The method according to claim 1 wherein the contaminant fraction consists of polars, aromatics, heteroatoms, unsaturates, and olefines.

19. The method according to claim 13 wherein the liquid/liquid extraction is under conditions wherein the extractant is at least partially miscible in the oil.

20. The method of claim 13 wherein the liquid/liquid extraction is undertaken between 140° F. and 200° F.

21. The method of claim 13 wherein the liquid/liquid extraction is undertaken with an extractant treat ratio in excess of 3:1 by volume.

22. The method of claim 13 wherein the liquid/liquid extraction is undertaken in an extraction column configured to provide a steeper vacuum at the flash zone.

23. The method of claim 13 wherein the liquid/liquid extraction is undertaken in a packed column.

24. The method of claim 11 wherein a residence time is for each stage is controlled from a central controller.

25. The method according to claim 11 whereby a phase catalyst is used to enhance extraction.

26. The method of claim 1 wherein the hydrogenation process comprises one or more of hydrotreating, hydrofinishing, alkylating, or molecular reforming.

27. A method for producing oils from waste oil, the method comprising:

a) controlling separation of at least a portion of material having a boiling point less than about 350° F. from feedstock to produce a de-volatized oil fraction and a light oil fraction using a central controller and automatically in response to a first sensor setting;

b) controlling separation of at least a portion of material with a boiling point greater than about 350° F. and less than about 650° F. from the de-volatized oil fraction to produce a fuel oil fraction and a heavy oil fraction using the central controller and automatically in response to a second sensor setting;

c) controlling separation of at least a portion of material with a boiling point greater than about 1200° F. from the heavy oil fraction to produce a partially purified oil fraction and a residual fraction using the central controller and automatically in response to a third sensor setting;
d) controlling treatment of the partially purified oil fraction to separate the partially purified oil faction into a purified oil fraction and a contaminant fraction using liquid/liquid extraction with extractant recovery processing, using the central controller and automatically in response to a fourth sensor setting;
e) controlling hydrogenation of the contaminant fraction and the fuel oil fraction to remove predetermined compounds, further saturating the contaminant fraction and thereby creating a saturated oil fraction, using the central controller and automatically in response to a fifth sensor setting; and
f) fractionating the saturated oil stream to produce one or more of a naphtha fraction, a diesel oil fraction and a base oil fraction; wherein controlling the separation of the portion of material with the boiling point greater than about 1200° F. comprises spraying cooled distillate from a vessel back into the vessel at a first predetermined location in a horizontal direction and in a second predetermined location in a vertical direction.

28. A method for producing oils from waste oil, the method comprising:
a) controlling separation of at least a portion of material having a boiling point less than about 350° F. from feedstock to produce a de-volatized oil fraction and a light oil fraction using a central controller and automatically in response to a first sensor setting;
b) controlling separation of at least a portion of material with a boiling point greater than about 350° F. and less than about 650° F. from the de-volatized oil fraction to produce a fuel oil fraction and a heavy oil fraction using the central controller and automatically in response to a second sensor setting;
c) controlling separation of at least a portion of material with a boiling point greater than about 1200° F. from the heavy oil fraction to produce a partially purified oil fraction and a residual fraction using the central controller and automatically in response to a third sensor setting;
d) controlling treatment of the partially purified oil fraction to separate the partially purified oil faction into a purified oil fraction and a contaminant fraction using liquid/liquid extraction with extractant recovery processing, using the central controller and automatically in response to a fourth sensor setting;
e) controlling hydrogenation of the contaminant fraction and the fuel oil fraction to remove predetermined compounds, further saturating the contaminant fraction and thereby creating a saturated oil fraction, using the central controller and automatically in response to a fifth sensor setting; and
f) fractionating the saturated oil stream to produce one or more of a naphtha fraction, a diesel oil fraction and a base oil fraction; wherein controlling the separation of the portion of material with the boiling point greater than about 1200° F. comprises spraying cooled distillate from a vessel back into the vessel at a location in which one or more chevrons are disposed.

* * * * *